United States Patent
Zhang et al.

(10) Patent No.: US 10,967,030 B2
(45) Date of Patent: Apr. 6, 2021

(54) TRADITIONAL CHINESE MEDICINE COMPOSITION FOR TREATING PSORIASIS AND METHOD FOR PREPARING THE SAME

(71) Applicant: Beijing Zhendong Guangming Pharmaceutical Research Institute Co., LTD, Beijing (CN)

(72) Inventors: Siju Zhang, Beijing (CN); Jinhua Wang, Beijing (CN); Wenjie Qin, Beijing (CN); Xiaoning Yang, Beijing (CN); Juanjuan Liang, Beijing (CN); Hongjiang Hao, Beijing (CN); Hongyu Wang, Beijing (CN)

(73) Assignee: Beijing Zhendong Guangming Pharmaceutical Research Institute Co., Ltd., Beijing (CN)

( * ) Notice: Subject to any disclaimer, the term of this patent is extended or adjusted under 35 U.S.C. 154(b) by 0 days.

(21) Appl. No.: 16/336,876

(22) PCT Filed: Sep. 27, 2016

(86) PCT No.: PCT/CN2016/100220
§ 371 (c)(1),
(2) Date: Mar. 26, 2019

(87) PCT Pub. No.: WO2018/058261
PCT Pub. Date: Apr. 5, 2018

(65) Prior Publication Data
US 2019/0247456 A1    Aug. 15, 2019

(51) Int. Cl.
| | |
|---|---|
| *A61K 36/70* | (2006.01) |
| *A61K 36/489* | (2006.01) |
| *A61K 36/80* | (2006.01) |
| *A61P 17/06* | (2006.01) |
| *A61K 36/71* | (2006.01) |
| *A61K 36/48* | (2006.01) |
| *A61K 36/282* | (2006.01) |

(52) U.S. Cl.
CPC .......... *A61K 36/70* (2013.01); *A61K 36/282* (2013.01); *A61K 36/48* (2013.01); *A61K 36/489* (2013.01); *A61K 36/71* (2013.01); *A61K 36/80* (2013.01); *A61P 17/06* (2018.01); *A61K 2236/333* (2013.01); *A61K 2236/51* (2013.01); *A61K 2236/53* (2013.01)

(58) Field of Classification Search
None
See application file for complete search history.

(56) References Cited

FOREIGN PATENT DOCUMENTS

CN    105982970 A    10/2016

OTHER PUBLICATIONS

He et al. (2015) J. Ethnopharmacology 172: 10-29. (Year: 2015).*
Website document entitled: "Rumex" (available at en.wikipedia.org/wiki/Rumex). Downloaded from website Feb. 7, 2020. (Year: 2020).*
Revilla et al. (1998) J. Agric. Food Chem. 46, 4592-4597. (Year: 1998).*
Raskin et al. (2004) Current Pharmaceutical Design, 10: 3419-3429. (Year: 2004).*
International Preliminary Report on Patentability corresponding to International Application No. PCT/CN2016/100220, dated Apr. 2, 2019.
Xu, Kerning, "Development and clinical application of Yinxieling Film Coating Agent", Chinese Journal of Traditional Medical Science and Technology, 2006, issue 3, p. 210, paragraphs, 2-3 in the left column, Jun. 30, 2006.
Hu, Wei, "Progress in the application of Traditional Chinese Medicine medicine bath in the nursing of psoriasis", Thesis Compilation of Academic Exchange Conference of National Traditional Chinese Medicine and Integrated Western and Chinese Nursing, p. 212, paragraphs 2-3, Dec. 31, 2011.

* cited by examiner

*Primary Examiner* — Russell G Fiebig
(74) *Attorney, Agent, or Firm* — Arent Fox LLP

(57) ABSTRACT

The invention relates to the field of traditional Chinese medicine, in particular to provides traditional Chinese medicine compositions for the treatment of psoriasis, their preparations and their preparation methods. The Chinese medicine compositions of the invention are consisted of 20-80 parts of *Rumex madaio,* 20-80 parts of Radix *sophora flavescens,* 10-50 parts of Herba *Siphonostegiae,* 10-40 parts of Chinese *pulsatilla chinensis,* and 5-30 parts of *Acacia catechu,* by weight. The invention also includes the preparation methods of the traditional Chinese medicine compositions and the preparations containing the traditional Chinese medicine compositions and method for preparing the same. The pharmacological experiments and clinical experiments proved that the traditional Chinese medicine compositions of the invention have remarkable curative effects on psoriasis vulgaris, high cure rate, no toxic and side effects of hormones, and is suitable for the characteristics of psoriasis having long-term use due to the long-course of the diseases.

5 Claims, 1 Drawing Sheet

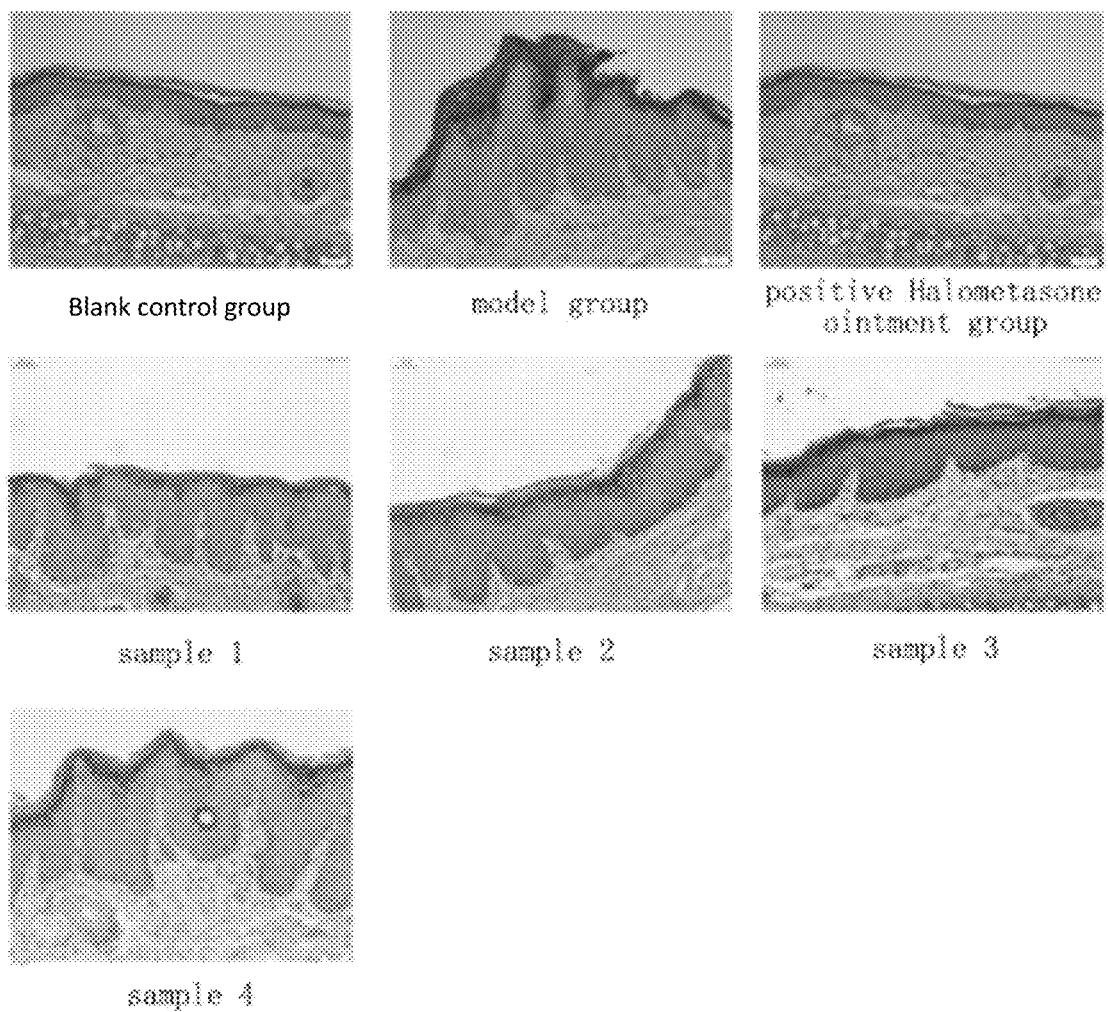

TRADITIONAL CHINESE MEDICINE COMPOSITION FOR TREATING PSORIASIS AND METHOD FOR PREPARING THE SAME

CROSS-REFERENCE TO RELATED APPLICATIONS

The present application is a U.S. National Stage Entry of International Application No. PCT/CN2016/100220, filed Sep. 27, 2016. The disclosure of the priority application is hereby incorporated herein in its entirety by reference.

FIELD OF THE INVENTION

The present invention relates to the field of traditional Chinese medicine, and in particular to traditional Chinese medicine compositions for treating psoriasis and preparations thereof and a method for preparing the same.

BACKGROUND OF THE INVENTION

Psoriasis is commonly referred to as cattle-skin lichen. The cattle-skin lichen in the Chinese medicine concept comprise a group of skin diseases in western medicine clinic, and also comprise neurodermatitis and eczematous skin diseases etc. it is not specifically referred to as Psoriasis. The record of psoriasis-like skin diseases in the motherland medicine was first seen in the "Treatise on the Causes and Manifestations of Diseases" of Chao Yuanfang in the Sui Dynasty, it was called "chronic eczema" and "white ringworm"; In the medical books of the Song, Ming and Qing dynasties, it was also called "corporic tinea", "Pine bark ringworm", "white mange" etc. It is essentially inaccurate that cattle-skin lichen is named Psoriasis, because the "stubborn and firm" rash is just one of the manifestations of psoriasis, but many characteristic rash manifestations of psoriasis, and histopathology, pathogenesis and genetics thereof, and so on, these aspects are fundamentally different from other skin diseases belonging to Psoriasis. The history of written records of Psoriasis is for more than 1400 years in China. So far, the basic cause of the disease is not still fully clear in the worldwide, and it is impossible to solve the problem of complete eradication and no longer relapse of the disease.

There are three main clinical features of psoriasis with diagnostic value, comprising: 1. wax drop phenomenon: the primary eruption is inflammatory papules or maculopapule having a size of from pinhead to hyacinth bean, being light red in color, and the papules can gradually expand or fuse with each other to form a plaque, having a clear boundary, mild redness at the periphery, and the surface covered with multiple layers of silvery-white scales which can be scraped off lightly as wax drops; 2. thin film phenomenon: after lightly scraping off the scales, there is a layer of reddish and light translucent film; 3. point-like bleeding phenomenon: after re-scraping off the thin film, the scattered small bleeding points may appear. Psoriasis has a long course of disease, rendering it impossible to quickly resolve the skin lesions, and leading to slow effect, and it is mostly heavy in winter and light in summer. The disease can occur throughout the whole body, and the predilection sites are the elbows, knees, head and extension of limbs, and which happens in a symmetry way. Epidermal hyperplasia and angiogenesis in the dermal papilla layer are the main pathological features of psoriasis, and genetic factors and environmental stimuli are the two major factors leading to paroxysm. The psoriasis has complex clinical manifestations, and is a multi-gene hereditary disease, involves some genetic polymorphisms of the immune system and keratinocyte abnormalities; its pathogenesis involves the following four major cell types: keratinocytes, lymphocytes, endothelial cells, and neutrophils, the former two are the most critical among them. It is considered by most scholars that psoriasis is a T cell-mediated chronic inflammatory disease, activated T lymphocytes have been confirmed to be present in the epidermis and dermis of psoriatic lesion, the activated T cells can release inflammatory factors and thus the inhibition of T cell activation may directly inhibit the formation of psoriatic lesions in normal skin; the immune-mediated theory based on T cells has become a hot spot for the studies of many scholars today.

The incidence of psoriasis increase in recent years, which is closely related to the environmental pollutions today, especially invading young adults, so it has a great impact on physical health and mental health of the patents. No radical cure for psoriasis has become a world problem in current dermatology, due to its high incidence, being difficult to cure during the long course of decades, easy relapsing after regression, and even lifelong enduring. Currently it becomes a world problem in dermatology that Psoriasis cannot be cured.

Psoriasis is easy to diagnose in the clinic. The current treatment methods mainly include three categories: external medicine, systemic treatment and physical therapy.

Professor Zhizhong Zheng, director of the dermatology department of Huashan Hospital of Fudan University considered that: external treatment of psoriasis vulgaris (which is about 95% of psoriasis) is dominant. Professor Ping Tu, dermatology department of Peking University First Hospital, also believed that topical treatment of psoriasis is the safest first-line treatment. The American Academy of Dematology (AAD) published the "Guidelines for the Treatment of Psoriasis by External Drugs" in 2009, indicating that the conditions in 80% of patients with psoriasis are mild to moderate, and higher efficiency and safety rate can be achieved by the treatment of external drugs only. The external drug is directly applied to the lesions through skin via plaster therapy, and the drug is absorbed into the blood circulation through the skin, thereby avoiding the adverse effects of first pass effect in liver and inactivation in gastrointestinal tract which may occur by oral administration, thereby improving the therapeutic effect. Currently most of the external drugs used in the treatment of psoriasis are western medicines, including: 1. glucocorticoid ointment preparations: halomethasone, betamethasone dipropionate, fluocinolone, mometasone furoate (Eloson), halcinonided, dexamethasone, hydrocortisone butyrate, etc.; 2. vitamin $D_3$ derivative ointment preparations: calcipotriene, tacalcitol, calcitriol, etc.; 3. retinoid gel or emulsion: all-trans retinoic acid, 13 cis-retinoic acid, tazarotene, etc.; 4. immunomodulators: methotrexate cytotoxic drugs, triptolide ointment and cyclosporin; 5. Tars: 1-5% coal tar, 5% pityrol, 6. cytotoxic drugs: 0.05% chlormethine hydrochloride solution; 7. anti-tumor drugs such as Aminopterin, methotrexate, Azathioprine, ethylenediamine etc. In addition, there are auxiliary therapeutic drugs such as emollients, keratoplastics, keratolytics, or the like. Although these drugs, especially glucocorticoids have an effect on psoriasis and some have a strong and fast effect, long-term and excess external use may cause systemic adverse reactions due to absorption of the drugs, in which some are very serious, such as skin atrophy, telangiectasia, secondary infections such as bacterial and fungi infections, even make skin lesion rebounding, aggravating, and converting into pustular psoriasis, and causing damages to the hematopoietic system and the liver. The traditional medical science in China is very broad and profound, and a task of top priority focuses on the development of excellent Chinese traditional medicines for the treatment of psoriasis. Up to now, pure traditional Chinese medical external preparations for the treatment of psoriasis which has the medicine permission number approved by the Center for Drug Evaluation of China Food and Drug Administration is precious few, drugs in clinical use are mostly hospital pharmacy preparations.

The Chinese traditional medicine is a great treasure house, it is believed in Chinese medicine that pathogenesis of psoriasis is mainly caused by the attack of foreign wind toxin and pathogenic factor due to internal factors such as blood-dryness, blood-heat, blood-insufficiency, blood-stasis. The modern times skilled doctors mostly venerate the views of the Ming and Qing dynasties, for example, Bingnan Zhao, Renkang Zhu, Mingqi Zhou and other famous veteran doctors of TMC believe that the blood-heat is the key factor in the paroxysm of psoriasis; overabundance of yang in the body combined with external assault by wind cause the paroxysm; and the long-lasting disease reduces the Yin-blood, resulting in yin deficiency and blood-dryness, as well as malnutrition of skin. There are internal therapies in the rehabilitation treatment of this disease: cleaning up tinea poison, driving away pathogen, driving out pathogen, harmonizing yingfen and weifen; external therapies: killing tineavenom, to fortify defenses and raze the fields (idiom). Nowadays, there are many Chinese medicine preparations for oral administration. "Keyin Pills" and "Keyin Formula" of well-known veteran doctors of TCM Professor Zhu Renkang, "Liangxue Jiedu Decoction" of Professor Bingnan Zhao, "Xiaoyin Mixture" of Professor Zhizhong Zheng, etc. Part One of Chinese Pharmacopoeia in 2005 Edition and 2010 Edition contained "Xiaoyin Tablets" and "Yinxie Capsules" successively, while in clinic, external Chinese medicine preparations approved by the Center for Drug Evaluation of China Food and Drug Administration are rarely found. It is a task of top to research and develop the traditional Chinese medicines for external use in accordance with the etiology and pathogenesis of psoriasis.

SUMMARY OF THE INVENTION

In view of the above technical circumstances, the present invention provides a traditional Chinese medicine compound recipe composition for treating psoriasis with a definite curative effect and small toxic side effects, preparations thereof, and a method for preparing the same.

The traditional Chinese medicine composition of the invention is mainly consisted of two traditional Chinese medicines, that is, *Rumex madaio* (*Rumex madaio* MakinoR. *daiwoo* Makino) and Radix *sophora flavescens* (*Sophora flavescens* Alt. Hort. Kew ed.), acting as the sovereign drugs, which is derived from the folk prescription, and *Rumex madaio* and Radix *sophora flavescens* are determined to be the sovereign drugs of the composition via the laboratory test and clinical pre-tests. In one embodiment of the present invention, the traditional Chinese medicine composition is consisted of 20-80 parts by weight of *Rumex madaio* and 20-80 parts by weight of Radix *sophora flavescens*; in one further embodiment, 30 to 70 parts of *Rumex madaio* and 30 to 70 parts of Radix *sophora flavescens*; in one further embodiment, 35 to 65 parts of *Rumex madaio* and 35 to 65 parts of Radix *sophora flavescens*; in one further embodiment, 40 to 60 parts of *Rumex madaio* and 40 to 60 parts of Radix *sophora flavescens*; in one further embodiment, 30 to 50 parts of *Rumex madaio* and 30 to 50 parts of Radix *sophora flavescens*.

The invention further provides a traditional Chinese medicine composition consisting of *Rumex madaio*, Rsdix *sophora flavescens* and Herba *Siphonostegiae* (*Siphonostegia chinensis* Benth.). In the present traditional Chinese medicine composition, *Rumex madaio* and Radix *sophora flavescens* act as the sovereign drugs, and Herba *Siphonostegiae* acts as the minister drug having the function of promoting blood circulation and removing blood stasis; in one embodiment of the present invention, the pharmaceutical composition consisting of *Rumex madaio*, Radix *sophora flavescens* and Herba *Siphonostegiae*, which is consisted of 20-80 parts of *Rumex madaio*, 20-80 parts of Radix *sophora flavescens*, and 10-50 parts of Herba *Siphonostegiae*, by weight; particularly 20-50 parts of *Rumex madaio*, 20-50 parts of Radix *sophora flavescens*, and 15-40 parts of Herba *Siphonostegiae*; in one embodiment, 30-50 parts of *Rumex madaio*, 30-50 parts of Radix *sophora flavescens*, and 20-40 parts of Herba *Siphonostegiae*. in one further embodiment, 25-45 parts of *Rumex madaio*, 25-45 parts of Radix *sophora flavescens*, and 20-35 parts of Herba *Siphonostegiae*.

The present invention further provides a traditional Chinese medicine composition consisting of *Rumex madaio*, Radix *Sophora flavescens*, Herba *Siphonostegiae*, Chinese *pulsatilla chinensis* (*Pulsatilla chinensis* (Bunge) Regel), and *Acacia catechu* (*Acacia catechu* (L.f.) Willd.). In one embodiment, the traditional Chinese medicine composition of the present invention is consisted of 20-80 parts of *Rumex madaio*, 20-80 parts of Radix *sophora flavescens*, 10-50 parts of Herba *Siphonostegiae*, 10-40 parts of Chinese *pulsatilla chinensis*, and 5-30 parts of *Acacia catechu*, by weight; in one further embodiment, 20-50 parts of *Rumex madaio*, 20-50 parts of Radix *sophora flavescens*, 15-40 parts of Herba *Siphonostegiae*, 10-40 parts of Chinese *pulsatilla chinensis*, and 10-30 parts of *Acacia catechu*; in one still further embodiment, wherein 20-40 parts of *Rumex madaio*, 20-40 parts of Radix *sophora flavescens*, 15-30 parts of Herba *Siphonostegiae*, 15-30 parts of Chinese *pulsatilla chinensis*, and 10-20 parts of *Acacia catechu*; one still further embodiment, 25-35 part of *Rumex madaio*, 25-35 parts of Radix *sophora flavescens*, 15-25 parts of Herba *Siphonostegiae*, 15-25 parts of Chinese *pulsatilla chinensis*, and 10-15 parts of *Acacia catechu*.

In the pharmaceutical composition of the present invention, *Rumex madaio* and Radix *sophora flavescens* are the sovereign drugs, and into which Herba *Siphonostegiae* as the minister drug having the effect of promoting blood circulation and removing blood stasis is added; and into which the Chinese *pulsatilla chinensis* as the assistant drug having the effect of clearing heat and removing toxicity and *Acacia catechu* as the envory drug having the effect of eliminating dampness and astring sores, promoting granulation and hemostasis are further added.

The present pharmaceutical compositions are directed to the most common cause of psoriasis vulgaris, selecting and using Chinese medicines having the effects of clearing heat and cooling blood, clearing heat and eliminating dampness, dispelling pathogenic wind and removing toxicity substance, promoting blood circulation for removing blood stasis, cooling blood for resolving macula, resolving static blood and detumescence, analgesia and removing itching, and clearing heart fire, in order to promote capillary expansion and improve the immune function of the body, thereby achieving the purpose of psoriasis treatment.

In one embodiment of the present traditional Chinese medicine compositions, the scientific name, function & indication and main substance basis (chemical compositions) of each medicine in the traditional Chinese medicine compositions are as follows:

Wherein the "*Rumex madaio*" is a dry root of commonly known as "*Rumex madaio*" having a variety of origins in the genus *Rumex* of Knotweed Family (Polygonaceae) plants, and includes wild and/or cultivated medicinal materials and their "prepared drug in pieces" and/or "processed products". It mainly includes 16 varieties of the genus that have a long history of drug administration, preferably the following five species, which have local standards, namely *R. patientia, R. crispus, R. nepalensis, R. dentatus* and *R. obtosifolius*. There are also *R. japonicus, R. acetosa, R. trisetifer, R. chalepensis, R. gmelinii,* and *R. stenophyllus, R. aquaticus, R. psedonatronatus, R. longifolius, R. tianschancus,* and *R. hastatus. R. patientia* and *R. crispus* are included in local standards in Beijing and Tianjin; *R. nepalensis* and *R. dentatus* are included in local standards in Guizhou; and *R. obtosifolius* is included in the local standard in Anhui.

*Rumex madaio* is cold in nature, bitter and pungent, channeling entry of heart and lung. Function & Indications: clearing heat and removing toxicity, cooling blood and hemostasis, clearing fire and relaxing bowels, promoting blood circulation and dissipating blood stasis, and destroying parasites and treating tinea. It can relax bowels and anti-diarrhoeal, treat hemafecia and other hemorrhage, constipation, upper respiratory tract infection, anti-asthma, heat removal etc. via internal administration in clinic; and it can treat Bald mustard tinea, destroying parasites, eczema, cattle-skin lichen, fungal infection and other skin diseases via topical administration. Main chemical components: free anthraquinone: emodin, chrysophanol, and emodin methyl ether; bounded form anthraquinone: emodin-8-O-β-D-glucopyranoside, emodin methylether-8-O-β-D-glucopyranoside, chrysophanol-8-O-β-D-glucopyranoside; flavonoids: kaempferol, kaempferol-3-O-α-L-mannopyranoside, quercetin, quercetin-3-O-α-L-mannopyranoside, catechin, epicatechin, musizin and its glycosides, resveratrol, etc.;

Wherein the "Radix *sophora flavescens*" is dry roots of the leguminous plant *Sophora flavescens* Ait., including wild and/or cultivated medicinal materials and their "prepared drug in pieces" and/or "processed products";

Radix *sophora flavescens*: cold in nature and bitter in taste, channel entry of heart, liver, stomach, large intestine, and bladder. Function & Indications: clearing heat and removing dampness, killing ascarid, and diuresis. It is used for heat dysentery, hemafecia, jaundice and urinary retention, red and white vaginal discharge, vulval swelling and pruritus vulvae, eczema, wet sores, itchy skin, mustard tinea and leprosy; and it can treat trichomonas vaginitis via external administration. Main chemical components: 34 kinds of alkaloids mainly comprising matrine, oxymatrine, oxidized sophocarpine, sophocarpine, sophoridine and cytisine; 85 kinds of flavonoids mainly comprising norkurarinone, kurarinone, and trifolirhizin, and 5 kinds of saponins.

Wherein the Herba *Siphonostegiae* is dry whole herbs of the genus *Scrophulariae* plant *Siphonostegia chinensis* Benth., including wild and/or cultivated medicinal materials and their "prepared drug in pieces" and/or "processed products".

Herba *Siphonostegiae*: cold in nature and bitter in taste, channel entry of spleen, stomach, liver, gallbladder. Function & Indications: promoting blood circulation and dissipate blood stasis, promoting menstruation and relieving pain, cooling blood for hemostasis, clearing heat and promoting diuresis, clearing fire and cold, and treating patients with blood stasis and fever. It is used for treating traumatic injury, external injury and hemorrhage, blood stasis and amenorrhea, menstrual disorders, postpartum pain with blood stasis syndrom, accumulation of gynecologic abdominal lumps, bloody flux, hematuric stranguria, jaundice due to dampness heat, edema and abdominal distention, excessive vaginal discharge. Main chemical components: flavonoids: 5,3'-dihydroxy-4',6,7-trimethoxyflavone, 5,7-dihydroxy-3,4-dimethoxyflavone, apigenin, apiin, luteolin, galuteolin etc. Quinic acid and ester thereof compounds: 3,4-dicaffeoylquinic acid, MaerantheinF, 3,4,5-tricaffeoyl quinic acid methyl ester. Coumarins: 7-methoxycoumarin, 7-hydroxycoumarin. Organic acids: isoferulic acid, trans-p-hydroxycinnamic acid, 1R, 2R, 4R-trihydroxy menthane and daucosterol.

Wherein the Chinese *pulsatilla chinensis* is dried roots of the *Pulsatilla chinensis* (Bge.) Regel of buttercup family plants, including wild and/or cultivated medicinal materials and their "prepared drug in pieces" and/or "processed products";

The Chinese *pulsatilla chinensis*: cold in nature and bitter in taste, channel entry of stomach and large intestine. Function & Indications: clearing heat and removing toxicity, cooling blood and checking flow field. It is clinically used for heat-toxicity and bloody flux, dripping yellow water, eczema, mustard and acne, wind-damp-heat, jaundice and reddish urine. Main chemical components: triterpenoids, triterpenoid saponins: dozens kinds of triterpenoid sapogenins and saponins in the form of lupinane and oleanane type (mainly hederagenin), coumarins: 4,7-dimethoxy-5-methylcoumarin. Organic acids: betulinic acid, betulonic acid. Cardiotonic ingredients: anemonin, raddeanin(anemodeanin) A, okinalin, okinalein and so on. Lignans: (+)-pinoresinol, podophyllum resin B, etc.

Wherein *Acacia catechu* is a dry decocting paste of a peeled branch and trunks of a leguminous *Acacia catechu* (L.f.) Willd., and/or "processed product" thereof.

*Acacia catechu*: bitter in taste, astringent, and slightly cold in nature, channel entry of lungs and heart meridians. Function & Indications: promoting blood circulation and relieving pain, hemostasis and promoting granulation, removing dampness and astringing sores, clearing lung-heat and resolving phlegm. It is used for treating hurt and pain due to stumble and fall, bleeding wound, hematemesis and bleeding from five aperture or subcutaneous tissue, astringing for sore and unler, eczema, wet sores, lung heat and cough. Main chemical components: mainly comprising flavonoids: catechin, epicatechin, kaempferol, quercetin, afzelechin, epi-afzelechin, kaempferol, 3, 4', 7'-trihydroxy-3', 5-dimethoxyflavone, catechin, epicatechin, dihydrokaempferol, etc.; phenol, 4-hydroxybenzoic acid, and the like.

The traditional Chinese medicine compositions of the present invention may constitute a plurality of compositions in a set weight parts, in one embodiment, said compositions may be extracted or refined to obtain "extracts" or "refined products" of the compositions; and then the "extracts" and "refined products" are used as the raw materials of various external or internal preparations, and the adjuvant materials are added to prepare various external or internal preparations.

In one embodiment, the traditional Chinese medicine compositions of the present invention can be prepared according to an "extraction process", wherein the "extraction process" includes the following steps:

Extraction step: the extraction solvent is water or 50-100% pharmaceutical ethanol solution; the extraction method comprises soak, reflux via heating, diacolation after maceration, ultrasonic extracting, microwave extracting, boiling or supercritical liquid extracting; wherein the time for soak is preferably 0.5 to 1.0 hours; the extraction times is 2 to 4 times, preferably 3 times; the time for extraction is 1.0 to 2.0 hours, and the total amount of solvent used for extraction is 15 to 20 L/Kg; in one embodiment of the present invention, before the extraction by water or alcohol, the crude medicinal materials of the components of the compositions of the present invention may be broken into coarse granules or flakes, and uniformly mixed according to the given parts by weight of the components, and then extracted.

Filtration step: settling separation under atmospheric pressure, pressurization or vacuum filtration, centrifugal separation, this step can remove the dregs, and obtain a clear extraction solution.

Concentration step: concentration under reduced pressure, thin film concentration, evaporation via thin film evaporator; in one embodiment, the concentration temperature is 60° C. or below; this step can obtain a concentrate of the compositions of the present invention.

Drying step: vacuum drying, spray drying, freezing drying or microwave drying; in one embodiment, the drying temperature is also preferably 60° C. or below.

Except for the active substances for treating psoriasis, the extracts of the traditional Chinese medicine compositions of the present invention obtained by the above methods, still contains a few of small molecule compounds such as monosaccharides, disaccharides, oligosaccharides or an inorganic salt, and macromolecular impurities such as pectin, mucilage, protein, and resin etc.

In order to further increase the content of the active ingredients, in one embodiment of the present invention, the extracts may be further refined. The refining may be carried out by a water extraction and alcohol precipitation method, an alcohol extraction and water precipitation method, macroporous adsorption resin chromatography method, a polyamide chromatography method, an ion exchange resin chromatography method or a membrane separation technique. After refining, the content of the "refined product" is about 35% of the total amount of the "extracts", since the treatment can remove the ineffective impurities in the extracts, and the active ingredients are saved maximumly and their contents are increased, thereby improving the drug efficacy. in one embodiment of the present invention, when the refining is carried out by a macroporous adsorption resin method, wherein the macroporous adsorption resin is selected from a non-polar, weakly-polar, medium-polar or polar resin, preferably AB-8, SP-825, D101, DM-130, HP-20, HPD100, HPD400, HPD600, X-5 or NKA-9 resin; preferably a medium-polar or weakly-polar resin; further preferably AB-8, X-5, SP-825, HPD400 or DM130;

In one embodiment of the present invention, when the extracts of the traditional Chinese medicine compositions of the present invention are refined by an ion exchange resin method, the resin is selected from a cation exchange resin, and preferably the resin is suitable for the alkaloids components contained in the compositions;

In one embodiment of the present invention, when the "extracts" of the traditional Chinese medicine compositions of the present invention are refined by polyamide chromatography method, materials having a size of 30 to 60 mesh are selected; in one embodiment of the present invention, when the "extracts" of the traditional Chinese medicine compositions of the present invention are refined by membrane separation method, the membrane separation technique should use an ultrafiltration membrane to intercept macromolecular pectin, mucilage, protein, resin and other organic impurities, and use a reverse osmosis membrane to intercept impurities such as small molecules sugars and inorganic salts.

In one embodiment of the present invention, the method for preparing the traditional Chinese medicine compositions comprises the following steps:

I) Preparation of the "extracts": individual components having corresponding weight parts are obtained respectively, broken into coarse grains or cutting into thin slices, and then mixed uniformly, The resulting mixture was immersed in a solvent of water or 50-100% pharmaceutical ethanol at about 40 degrees for about 0.5 to 1 hour, and then it was extracted for three times by heating reflux etc. (as an illustrative example, 8 times, 6 times, 6 times (L/kg) of solvent may be used), each extraction time is for 1-2 hours, the total amount of solvents is 15-20 (L/kg). The reflux solution is subjected to sedimentation separation under atmospheric pressure, and treated by one or two of suction filtration or centrifugation (4000 rpm, 30 min) method to obtain the extract solution, then solvents in the extract solution are recovered via evaporation and concentration under reduced pressure or film concentration at 60° C. or below to obtain a concentrate. The concentrate is dried under vacuum at 60° C. or below to provide an "extract";

II) Preparation of "refined products":

(A): Refining method of "extracts" obtained by using 50-100% pharmaceutical ethanol as solvent: "extracts" are treated by water sedimentation method, and the water-insoluble "precipitates" after treatment are dried under vacuum and stored. The remaining aqueous solution is separated by any one of macroporous adsorption resin columns selected from AB-8, X-5, SP-825, HPD400 or DM130 or polyamide chromatography columns of 30-60 mesh to remove impurities such as sugars and inorganic salts etc., The resin column diameter-length ratio is 1:6-1:10, and the elution is performed with water at a flow rate of 2-9 BV/h, to remove impurities such as small molecules sugars, inorganic salts and macromolecular pectin, mucilage, resin, polysaccharide and protein, etc., until the impurities such as sugars are washed away, and discarded. Further gradient elution is performed with 5%-80% ethanol, at a flow rate of 3-10 BV/h, finally, the column is eluted with 95%-100% ethanol to wash away adsorbate, the eluent is collected, and concentrated under reduced pressure, further dried under vacuum and combined with the aforementioned water-insoluble "precipitates", the "refined products" are obtained; or (B) A refining method of the "extracts" using water as solvent: after "water extracts" are precipitated with several times of ethanol to provide "alcohol precipitate", which are mainly impurities such as macromolecular pectin, mucilage, protein, resin and polysaccharides and thus are discarded. The alcohol-soluble portion are purified by macroporous resin adsorption method, polyamide chromatography method, or membrane separation techniques to remove impurities such as small molecules monosaccharides, disaccharides, oligosaccharides, and inorganic salts. The solvent ratio and diameter-length ratio of the resin column during refining using macroporous resin adsorption method are 1:6 to 1:10. in one embodiment of the present invention, when separation is carried out by polyamide chromatography, the alcohol-soluble portion concentrated to a small volume may be repeatedly dissolved in water to obtain two parts, that is, water-soluble substance and a water-insoluble substance, and the water-insoluble substance is directly dried under reduced pressure, and stored in another vessel; the water-soluble substance is separated by a polyamide chromatography column, eluted with water as a solvent, and real-time detected until there is no sugars, then eluted gradiently with different concentrations of pharmaceutical ethanol, and finally washed with 95%-100% ethanol to remove the adsorbates from the column. The ethanol eluate is collected, and concentrated by the above-mentioned methods including concentration under reduced pressure, or concentration by a thin film, and dried under reduced pressure to obtain a "refined products". in one embodiment of the present invention, when applying the membrane separation technique, an ultrafiltration membrane is used to intercept macromolecular impurities such as pectin, mucilage, protein, and resin, and then a reverse osmosis membrane is used to intercept small molecule impurity components such as sugars, inorganic salts, and the like in the extracts to give a "refined products".

In one embodiment, the "extracts" or "refined products" of the pharmaceutical compositions of the present invention can be used as raw materials to prepare a plurality of external preparations or internal preparations, wherein the external preparations include, but are not limited to, gel, ointment, cream, film coating agent, powder for topical application, lotion, liniment, paste, aerosol, spray or plaster; and the internal preparations include, but are not limited to, tablet, granule, powder, pill, capsule, syrup, dropping pill, fluid extract and extract or medicinal tea.

In one embodiment of the present invention, the adjuvant of the water-soluble matrix mainly used for the gel, ointment or cream in the external preparation includes: carbomer, glycerin gelatin, starch glycerin, cellulose derivative, polyethylene glycol, alginate, gum tragacanth, gelatin starch or any combination thereof, preferably carbomer gel matrix; alternatively, comprises water-insoluble matrix or water-insoluble matrix in combination with water-soluble matrix. The matrix of the said film coating agent comprises polyvinyl alcohol (PVA), polyvinyl formal-acetal, polyvinyl pyrrolidone, carboxymethyl chitosan or carbomer, or any combination thereof; plasticizers include glycerin, propylene glycol or dibutyl phthalate, or any combination thereof.

The preparations prepared by the present invention should comply with the relevant regulations of the Chinese Pharmacopoeia, and in one embodiment of the present invention, it is preferably in accordance with the requirements according to the General Rule of Preparation Appendix I of the 2010 edition of the Chinese Pharmacopoeia.

In one embodiment of the present invention, when the preparations of the pharmaceutical compositions is gel, the water-soluble matrix of the gel comprises: carbomer, glycerin gelatin, starch glycerin, cellulose derivative, polyethylene glycol, alginate, tragacanth or any combination thereof; preferably a carbomer gel matrix;

In one embodiment of the present invention, when the preparations of the pharmaceutical compositions of the present invention is a film coating agent, the matrix of the film coating agent includes polyvinyl alcohol (as an illustrative description, for example, PVA124, 1750 or 1788), polyvinyl formal-acetal, polyvinyl pyrrolidone, acrylic resin, carbomer or carboxymethyl chitosan. The plasticizer is glycerin, propylene glycol or dibutyl phthalate, or any combination thereof;

In one embodiment of the present invention, when the preparations of the pharmaceutical compositions of the present invention is an ointment or a cream, the water-soluble matrix of the ointment or cream comprises: glycerin gelatin, starch glycerin, cellulose derivative, polycarboxylate ethylene, alginate, tragacanth or polyethylene glycol, or any combination thereof. The oil-soluble matrix may be select from glyceryl monostearate, polyoxyl stearate (40), myristate, white petrolatum or beeswax, or any combination thereof, it is prepared by a conventional method for preparing an ointment or a cream.

As an illustrative example, the traditional Chinese medicine compositions of the present invention comprising 35 parts of *Rumex madaio,* 35 parts of Radix *sophora flavescens,* and 30 parts of Herba *Siphonostegiae* by weight, in which the three medicinal materials or prepared drug in pieces are moderately pulverized into coarse grains or cut into slices, and is processed by the method according to the present invention to obtain the "refined products", then the "refined products" is used as a raw materials for the preparations, and prepared to obtain gel by the following method. 50 ml distilled water is added to 2 g carbomer-980 in order to swell completely, and is stirred by blender. Triethanolamine is added to regulate pH value to around 4.0; another the "refined products" of the present compositions is filtered through 100 mesh sieve and served as a drug. 10 g the drug is dissolved in 10 g 95% ethanol, 30 g propylene glycol and 5 g humectant glycerin. the above mixture solution is added to Carbomer 980 in batches with stirring, then 0.5 g fine powder of Ethylparaben is dissolved in 5 g propylene glycol by ultrasound, then added to the matrix with stirring, followed by adding transdermal absorbent Laurocapram to said matrix with stirring uniformly in the same direction, finally, under stirring the same direction, the pH value is adjusted with triethanolamine to about 7.0, and supplemented with of purified water to 100 ml.

In the present invention, the said ointment, cream, and gel are a semi-solid preparations prepared by a mixture of drug and matrix for external application which is easily applied to the skin, mucous membrane or wound. The emulsion-type matrix is also a cream; and the water-soluble matrix is consisted of a natural or synthetic macromolecule water-soluble substance, which generally comprises glycerin gelatin, starch glycerin, cellulose derivatives, carboxy polymethleme and polyethylene glycol, and the like, or any combination thereof. The exemplary preparation method comprises: selecting a highly viscous CMC-Na, adding glycerin, well mixing, then adding an appropriate amount of purified water, standing said mixture in order to swell into a gel, then the above raw material solution, aqueous solution of Ethylparaben, the transdermal absorber and the antioxidant are added to gel in batches with stirring, continuous stirring is conducted to completely uniform mixing. The matrix can release drug fast, it is non-greasy, easy to spread, easy to wash, non-irritating to the skin and mucous membrane, and can mix with aqueous solution and absorb tissue exudate, so it is mostly used for moisturizing and anabrotic wound surface, which is beneficial to removing of secretions, being particularly suitable for the treatment of patients with psoriasis.

Preparations of the pharmaceutical compositions of the present invention can be prepared by those skilled in the art according to the ordinary knowledge in the art.

As one of the embodiments of the present invention, the gel is prepared by the following preparation method:

The "extracts" or "refined products" of the traditional Chinese medicine compositions of the present invention is pulverize into fine powder; appropriate amount of carbomer is weighed, and immersed in distilled water for 24 hours until it is completely swollen, to provide 2%-3% carbomer transparent gel, it is transferred to blender for full process stirring, and triethanolamine is dropped to adjust the pH value to 3.5-4, Alternatively, if necessary, the pH value of the carbomer can be adjusted firstly or lately; another fine powder of the "extracts" or "refined products" is added to carbomer gel in batches, or dissolved in propylene glycol and ethanol (where ethanol is controlled at 10% or less) and then added to the carbomer gel in batches and stirred evenly, the fine powder of preservative ethylparaben is dissolved in propylene glycol by ultrasound, and it was added in the mixture, then humectant glycerol, antioxidant sodium thiosulfate, and transdermal absorption agent laurocapram, etc. are added and stirred evenly. Triethanolamine is added to the mixture to adjust the pH value to 7 after the mixture is stirred uniformly, the stirring is conducted in the same direction until a viscous gel is formed, and obtained, in the preparations of "extracts" or "refined products" gel preparations, the content of "extracts" in the preparations using the "extracts" as raw material drug can be 20%-30%; and the content of refined products in the preparations using the refined products as the raw material drug can be 10%-20%.

In one embodiment of the present invention, the translucent gel preparations can be prepared according to the following method: The Chinese medicine compositions of the present invention or the "extracts" or "refined products" of the compositions are added and mixed with polysorbate 80, polyethylene glycol 400 and glycerin, and dissolved under heating. Sodium carboxymethyl cellulose and xanthan gum are dissolved in 80 ml of water, heated to 85° C. and gradually added to the solution of the "extracts" or "refined products" of the above compositions or traditional Chinese medicine compositions, to which a transdermal absorbent azone, propylene glycol solution of a fine powder of preservative Ethylparaben, and an antioxidant sodium thiosulfate are added to 100 ml with stirring uniformly, and cooled at room temperature to obtain a semi-transparent gel.

In one embodiment of the present invention, the said dermatological film coating agent is prepared according to the following preparation method: the film-forming materials such as PVA124, PVA1750, PVA1788, polyvinyl formalacetal or any combination thereof is added to purified water or 80% ethanol, in order to be soaked in a water bath at 80° C. and fully swelled into a light yellow semi-fluid liquid, it is transferred to a blender for full process stirring, and then added appropriate amount of diethyl phthalate plasticizer and mixed evenly to provide (1) liquid; another the traditional Chinese medicine compositions or the "extracts" or "refined products" of the pharmaceutical compositions is used as a raw material drug, and pulverized into a very fine powder, and dissolved in propylene glycol-ethanol, it is added to the (1) liquid in batches, and uniformly mixed; then ethylparaben preservative in propylene glycol, moisturizing agent, and antioxidant are added to the mixture, stirred uniformly, stood until there is not bubbles, loaded into a glass bottle in divided dosages, and sealed and obtained;

In one embodiment of the present invention, the ointment or cream is prepared by the following method: the present traditional Chinese medicine compositions, the "extracts" or "refined products" of the compositions as a raw material drug is pulverized into a very fine powder, the appropriate amount of propylene glycol-ethanol is added to dissolve said very fine powder and standby as (1) solution. Additionally, the oil-phase matrix selected from stearic acid, glyceryl monostearate, liquid paraffin, azone, and the aqueous-phase matrix selected from glycerin, water-soluble lanolin and Ethylparaben are heated to 80° C. respectively, and the aqueous-phase matrix is added to the oil-phase matrix under stirring from blender, then is cooled to 40° C., the above (1) liquid is added in batches and stirred well, and then the preservative ethylparaben, antioxidant and percolation agent is added and continuously stirred until completely uniform, and obtained; alternatively, regarding patients suffering from psoriasis with erosion wound for the purpose of being more conducive to absorbing tissue exudate, when water-soluble matrix is used, which generally comprises glycerin gelatin, a cellulose derivative (CMC-Na), poly or/and ethylene glycol; the said preparation method comprises: CMC-Na with high viscosity is selected and mixed well with glycerol, adding proper amount of purified water, then mixing evenly, stand it until it is dissolved into gel, and then adding the above the raw material drug solution, aqueous solution of ethylparaben, transdermal absorbent and antioxidant in batch, and continuously stirring until it is completely uniform, and obtained;

As an example for illustration, other external preparations such as external powders can be prepared by the following method in the present invention: the "extracts" or "refined products" of the traditional Chinese medicine compositions as a raw material drug are respectively pulverized into fine powder, sealed and packaged in divided dosages, and obtained.

The tincture is a clear liquid preparations prepared by leaching or dissolving a drug with a predetermined concentration of ethanol, also may be prepared by diluting with a flow extract. As an example for illustration, it can be prepared by the following method: taking any one of the above traditional Chinese medicine compositions, the method of the present invention: (1) impregnation method: the traditional Chinese medicine compositions of the present invention are pulverized into fine powder and mixed well, then impregnated for 48 hours in 60% ethanol as a solvent, followed by slow diacolation, the appropriate amount of diacolation solution collected and it's alcohol content it is adjusted to 60%, stirred evenly, and filtered and obtained. (2) dissolving method: each of the Chinese medicine compositions of the present invention is impregnated in 70% ethanol as a solvent for 2 hours, then heated and refluxed for 1.5 hours, the drug residue is refluxed with 70% ethanol twice, and filtered, collecting the filtrate for three times, said filtrate is concentrated in an appropriate amount, and adjusted to a specified amount with 70% ethanol and water, in order to reach the content of ethanol to 60%-65%, filtered and obtained.

When the compositions of the present invention is formulated into an internal preparations, in one embodiment of the present invention, methods for preparing granules include, but not limited to the following: (1) extracting: extracting a prescription drug via suitable solvent (water and 50%-95% ethanol), when water extraction is conducted, the water extract is concentrated at 60° C. or below to a concentration, and completely precipitated with 95% ethanol; the supernatant is concentrated at 60° C. or below to a thick paste, and standby; (2) granulating: the appropriate amount of dry sugar powder or other excipients are added to the above concentrated thick paste, and mixed well, soft materials are made by 70% ethanol as humectant, and then granulated with 12-14 mesh sieve on a granulator; (3) drying: wet particles are dried at a low temperature in oven.

In one embodiment, the preparation method of the granules further comprises: the "extracts" or "refined products" of the traditional Chinese medicine compositions of the present invention as raw material drug are pulverized into a fine powder of 80-160 mesh; and then prepared into granules using oligomerization lactose or dextrin as molding excipients, and prepared the granule by spray drying techniques and dry granulating techniques;

In one embodiment of the present invention, methods for preparing tables include, but not limited to the following: the "extracts" or "refined products" of the traditional Chinese medicine compositions of the present invention as a raw material drug is pulverized into fine powder of 80-160 mesh, to which the appropriate amount of excipients (hydroxypropyl cellulose, hydroxyl-β-cyclodextrin etc.) is added, and ethanol is used as humectant, the granulated, dried under reduced pressure (50-70° C.), tableted and coated, obtained;

In one embodiment of the present invention, methods for preparing capsules include, but not limited to the following: the "extracts" or "refined products" of the traditional Chinese medicine compositions of the present invention as raw material drug is pulverized into fine powder of 80-160 mesh, to which 1-2% of methyl cellulose, silicone or hydroxyethyl cellulose and other adjuvant materials is added, so that the powder has good fluidity, to ensure that the powder is quickly and accurately filled into gelatin hard capsules the filling of the drug is required to be carried out under the environment with about 25° C. and 35% to 45% relative humidity.

In one of the embodiments of the present invention, methods for preparing powder include, but not limited to the following: the "extracts" or "refined products" of the traditional Chinese medicine compositions of the present invention as raw material drug is pulverized into fine powder of 80-160 mesh, sieved and mixed evenly and obtained.

The flow extract, extract is a liquid dosage made from a medicinal material by leaching active ingredients with suitable solvent, and the solvent is evaporated partly, and adjust the concentration to a predetermined standard. It can be prepared by dipping, diacolation, or semi-countercurrent and multi-stage leaching process. As an Exemplary illustration, the present invention can be prepared by the following method. Method: taking the extracts of individual compositions with water or 50-95% ethanol as a solvent and obtained.

The pharmaceutical compositions of the present invention can be used not only for external administration, but also for internal administration, the lesion is treated by external use ointment, and by oral administration the internal medicine is used for consolidating the curative effect and preventing recurrence. The "extracts" or "refined products" of the compositions of the present invention and the preparations thereof are demonstrated to have significant effects in treating psoriasis vulgaris by pharmacological efficacy test and clinical pre-test, and have high cure rate and no hormonal side effects, and thus are suitable for the requirement of long-term use due to the long term of psoriasis pathogenesis.

DRAWINGS

FIG. 1 is a graph showing the results of observation under light microscopy after treatment of the pharmaceutical compositions and the control preparations of the present invention.

DETAILED DESCRIPTION

The present invention is further illustrated by the following examples and experimental examples, but the invention is not to be limited.

Preparation of Traditional Chinese Medicine Compositions

Example 1

Components (Parts by Weight): Rumex madaio 700 g, Radix sophora flavescens 300 g;

Method:

The above two Components were separately broken and well mixed based on said weight, and refluxed with 50% pharmaceutical ethanol having 8 times, 6 times, 6 times of total weight of the components to extract for 3 times, in which the first extraction was 2 hours, and each of the $2^{nd}$ and $3^{rd}$ extraction was 1.5 hours. The three extract solutions were combined, separated by sedimentation, and filtered with several layers of gauze, the turbid part at the bottom was centrifuged, and the extract solution was concentrated to a thick paste at 60° C. or below under reduced pressure, and the thick paste was dried in a vacuum dryer to obtain the "extracts".

Example 2

Components (Parts by Weight): Rumex madaio 600 g, Radix sophora flavescens 400 g Method:

The above two Components were separately broken, well mixed according to the weights, and refluxed with 70% pharmaceutical ethanol having 8 times, 7 times and 5 times of total weight of the components to extract for 3 times, in which the $1^{st}$ extraction was 2 hours, and each of the $2^{nd}$ and $3^{rd}$ extraction was 1.5 hours. The three extract solutions were combined, separated by sedimentation, and filtered with nylon cloth. The turbid part at the bottom was centrifuged to separate, and the extract solution was concentrated to an alcohol-free thick paste at 60° C. or below under reduced pressure, the thick paste was repeatedly dissolved in water, the water-insoluble portion was dried and then stored; and the water-soluble portion was separated by AB-8 macroporous adsorption resin which the diameter-length ratio of the resin column is 1:8, and the column was first eluted with water at 4-8 BV/h, until the impurities such as saccharides were washed away and discarded. The column was further gradiently eluted with 5%-80% ethanol at a flow rate of 2-10 BV/h, finally the adsorbates in the column was washed away with 95%-100% ethanol, and the eluate was collected, concentrated under reduced pressure, dried under vacuum and combined with the aforementioned "water-insoluble dry matter" to provide the "refined products". The "refined products" can be used as a raw material drug for various external or internal preparations.

Example 3

Components (Parts by Weight): Rumex madaio 350 g, Radix sophora flavescens 650 g Method:

The above two components were separately broken, well mixed according to the weight, and refluxed with purified water having 8 times, 6 times, 6 times of total weight of the components to extract for 3 times, in which the $1^{st}$ extraction was 2 hours, and each of the $2^{nd}$ and $3^{rd}$ extraction was 1.5 hours. The three extract solutions were combined, separated by sedimentation, and filtered, the extract solution was concentrated to a thick paste at 60° C. or below under reduced pressure, and the thick paste was dried in a vacuum dryer to obtain the "extracts".

Example 4

Components (Parts by Weight): Rumex madaio 300 g, Radix sophora flavescens 450 g, Herba Siphonostegiae 250 g Method:

The above three components were separately broken, and well mixed according to the weight, and refluxed with 60% pharmaceutical ethanol having 8 times, 7 times, 5 times of total weight of the components to extract for 3 times, in which the extraction time were 2 hours, 1.5 hours, and 1 hour, respectively, the three extract solution were combined, separated by sedimentation, and filtered with several layers of gauze, the turbid part at the bottom was centrifuged, and the extract solution was concentrated to a thick paste at 60° C. or below under reduced pressure, and the thick paste was dried in a vacuum dryer to obtain the "extracts".

Example 5

Components (Parts by Weight): *Rumex madaio* 400 g, Radix *sophora flavescens* 300 g, Herba *Siphonostegiae* 200 g Method:

The above three components were separately broken, and well mixed according to the weight parts, pulverized into fine powder, sieved, mixed, pelletized with 20-30 g of refined honey and an appropriate amount of water per 100 g of powder, and dried, to make water-honeyed pill.

Example 6

Components (parts by weight): *Rumex madaio* 350 g, Radix *sophora flavescens* 350 g, Herba *Siphonostegiae* 300 g Method:

The above three components were separately broken, well mixed according to the weight parts, and refluxed with 70% pharmaceutical ethanol having 8 times, 6 times, 6 times of total weight of the components to extract for 3 times, in which the $1^{st}$ extraction was 2 hours, and each of the $2^{nd}$ and $3^{rd}$ extraction was 1.5 hours. The three extract solutions were combined, separated by sedimentation, and filtered, the extract solution was concentrated to a thick paste at 60° C. or below under reduced pressure. The thick paste was repeatedly dissolved in water, the water-insoluble portion was dried and then stored in another vessel; and the water-soluble portion was subjected to chromatography on a polyamide column (the diameter-length ratio of the resin column is 1:8), the column was firstly eluted with water at 8-2 BV/h, and the eluate was real-time detected until there was no saccharide detected, and discarded. The column was further gradiently eluted with 5%-80% pharmaceutical ethanol, finally, the adsorbate in the column was washed away with 95%-100% ethanol, and the eluate was collected, concentrated at 60° C. or below under reduced pressure, vacuum dried at 60° C. or below and combined with the aforementioned "water-insoluble dry matter" to provide the "refined products".

Example 7

Components (Parts by Weight): *Rumex madaio* 350 g, Radix *sophora flavescens* 250 g, Herba *Siphonostegiae* 150 g, Chinese *pulsatilla chinensis* 150 g, *Acacia catechu* 100 g Method:

The above five components were broken respectively, and mixed according to the weight parts, and refluxed with 70% pharmaceutical ethanol having 8 times, 6 times and 6 times of total weight of the components to extract for 3 times, in which the $1^{st}$ extraction was 2 hours, and each of the $2^{nd}$ and $3^{rd}$ extraction was 1.5 hours. The three extract solutions were combined and separated by sedimentation and filtered, and the extract solution was concentrated at 60° C. or below under reduced pressure to free of alcohol, precipitated with several times amount of purified water to obtain "water-precipitation substance" and "water-soluble substance". The "water-precipitation substance" was vacuum dried and preserved; and the "water-soluble substance" was passed through the AB-8 or SP-825 macroporous adsorption resin column having a diameter-length ratio of 1:6 to 1:10. The column was firstly eluted with water at a flow rate of 2-9 BV/h, so as to remove impurities such as saccharide and inorganic salts. The column was then gradiently eluted with 5%-100% ethanol at a flow rate of 3-10 BV/h, the eluate was collected, concentrated under reduced pressure, dried under vacuum and combined with the aforementioned "water-precipitation substance" to obtain the "refined products".

Example 8

Components (Parts by Weight): *Rumex madaio* 300 g, Radix *sophora flavescens* 300 g, Herba *Siphonostegiae* 200 g, Chinese *pulsatilla chinensis* 150 g, *Acacia catechu* 50 g Method:

The above five components were broken respectively, and well mixed according to the weight parts, refluxed with purified water having 8 times, 6 times and 6 times total weight of the components to extract for 3 times, in which the extraction time was 2 hours, 1.5 hours, and 1.5 hours, respectively, the extracts were combined and separated by sedimentation, and then filtered with several layers of gauze, the turbid part at the bottom was centrifuged, and the extract was concentrated at 60° C. or below under reduced pressure to a thick paste, the thick paste was dried in a vacuum dryer to provide the "extracts".

Example 9

Components (Parts by Weight): *Rumex madaio* 250 g, Radix *sophora flavescens* 250 g, Herba *Siphonostegiae* 200 g, Chinese *pulsatilla chinensis* 200 g, *Acacia catechu* 100 g Method:

The above five components were separately broken, and well mixed according to the weight parts, refluxed with 80% pharmaceutical ethanol having 8 times, 6 times and 6 times of total weight of the components to extract for three times, in which the extraction time was 2 hours, 1.5 hours, and 1.0 hour respectively, the three extracts were combined, and separated by sedimentation, and then filtered with several layers of gauze, the turbid part at the bottom was centrifuged, and the extract was concentrated at 60° C. or below under reduced pressure to a thick paste, the thick paste was dried in a vacuum dryer to provide the "extracts"

Preparation of the Preparation

Example 10 Preparation of Gel (Two Components)

Raw Material Preparation:

30 g the raw material drug (extracts) from Example 1 were pulverized and passed through a 100 mesh sieve.

Preparation of the Preparations:

2 g carbopol-974 was selected as the gel matrix, and in which 50 ml of purified water was added, and swelled for 24 hours, then were adjusted pH value to 4 with triethanolamine, and evenly stirred with blender. 30 g of the "extract" powder from Example 1 was dissolved in 40 ml of propylene glycol, 5 ml of glycerin and 5 ml of ethanol, and added into the above carbomer gel matrix under stirring. 4% transdermal absorbent laurocapam and 3‰ ethylparaben preservative (finely ground), and 3‰ sodium thiosulfate antioxidant were added under stirring, the pH value was adjusted to 7 by triethanolamine, and uniformly stirred in the same direction to prepare a uniform and fine hydrophilic gel.

Example 11 Preparation of Gel (Three Components)

Raw Material of the Preparations:
10 g of the raw material "refined products" from Example 6 was pulverized and passed through a 100 mesh sieve.
Preparation of the Preparations:
3 g of sodium alginate was selected, and to which 50 ml purified water was added, and swelled to a viscous gel. The fine powder of "refined products" was dissolved in 35 ml of propylene glycol and 10 ml of glycerin, and stirred evenly in a mixer; then 3‰, finely ground ethylparaben preservative ultrasonically dissolved in 5 ml of propylene glycol were added, further 3‰ laurocapam transdermal absorbent was added, and stirred evenly in the same direction, then the viscous gel of alginate was slowly added and mixed uniformity under even stirring in a mixer.

Example 12 Preparation of Gel (Five Components)

Raw Material of the Preparations:
30 g of the "extracts" from Example 8 was pulverized and passed through a 120 mesh sieve.
Preparation of the Preparations:
30 g of above raw material drug powder, 2 ml of polysorbate 80, 10 g of polyethylene glycol 400 and 40 ml of propylene glycol were mixed, heated to 80° C., in order to form a transparent solution, stirred evenly by a blender, and then all of 3‰ preservatives Ethylparaben and 3‰ laurocapam were added under stirring. Further, 1 g of xanthan gum and 2 g of sodium carboxymethyl cellulose were dissolved in 45 ml of water, heated to 85° C. to make a matrix solution, gradually added to the above drug solution under stirring, finally added water to reach 100 ml, and cooled at room temperature to provide a translucent gel.

Example 13 Preparation of Film Coating Agent

Raw Material of the Preparations:
The "refined products" from Example 2 was used as a raw material drug, and passed through a 120 mesh sieve.
Preparation of the Preparations:
PVA17-88 (concentration: 10%) and carbopol-940 were placed in two beakers respectively. PVA17-88 was swollen in 5 times weight of purified water, and carbopol-940 was swollen in 60% ethanol under magnetic stirring, then they were respectively swelled into mucilage in the water bath of 90° C. (until there is no block visible), and filtered with gauze, standby. Glycerin, Tween-80 and ethyl 4-hydroxybenzoate were added into ethanol and stirred to dissolve, added to the fine powder of the above raw material in batches under stirring, stirred evenly, then added the mucilage of PVA17-88 and carbopol-940, stirred evenly, added ethanol and purified water to full amount, added triethanolamine solution to adjust the pH value to 7, and ultrasonically shaked until there is no bubbles.

Example 14 Preparation of Tablets

Raw Material of the Preparations:
the "extracts" from Example 8 was used as a raw material drug.
Method of the Preparations:
the dried extracts were pulverized to 100-120 mesh, evenly mixed with an appropriate amount of starch, granulated, dried and then tableted to provide tablets.

Example 15 Preparation of Granules

Raw Material of Preparations:
the "extracts" from Example 4 was used as raw material drug.
Preparation Methods:
the dried "extracts" from Example 4 is pulverized and passed through an 80 mesh sieve, to provide a "dry extract powders" and standby; the said "dry extract powders" and dextrin were mixed in a weight ratio of 2:1, added 85% ethanol as a wetting agent at a weight of 30% of total weight of the said dry powders and dextrin, further added stevioside at a weight of 2% of total weight of the said dry powder and dextrin, processed to soft material, sieved through 16 mesh, granulated, dried at 50° C., processed granulation, and split charged to provide finished products of granulates.

Test 1. Comparative Study of the Therapeutic Effects of Samples 1-4 on Experimental Psoriasis Model Via Topical Administration Preparation of samples: the dried powders of the four samples 1-4 (each sample comprising the specific components and proportion thereof, please see Table 1) were weighed, formulated into thick paste with propylene glycol before the experiment, and to which the appropriate amount of transdermal absorption promoter was added.

TABLE 1 components and proportions in the tested samples 1-4 (refined substance)

| Name of samples | Rumex madaio (Parts) | Rsdix sophora flavescens (Parts) | Herba Siphonostegiae (Parts) | Chinese pulsatilla chinensis (Parts) | Acacia catechu (Parts) |
|---|---|---|---|---|---|
| Sample 1 (Refined products from *Rumex madaio*) | 100 | | | | |
| Sample 2 (Refined products from Example 2) | 60 | 40 | | | |
| Sample 3 (Refined products from Example 6) | 35 | 35 | 30 | | |

TABLE 1-continued components and proportions in the tested samples 1-4 (refined substance)

| Name of samples | Rumex madaio (Parts) | Rsdix sophora flavescens (Parts) | Herba Siphonostegiae (Parts) | Chinese pulsatilla chinensis (Parts) | Acacia catechu (Parts) |
|---|---|---|---|---|---|
| Sample 4 (Refined products from Example 7) | 35 | 25 | 15 | 15 | 10 |

Note:
1) preparation method of Sample 1 is the same with Sample 2.
2) Sample 1 is acted as a control of single drug from *Rumex madaio*.

1.1 Effect of Samples 1-4 on Psoriasis-Like Skin Lesion Model of Guinea Pig Auricular Skin Induced by Propranolol Hydrochloride Sixty guinea pigs (weight 300-350 g), half male and half female, according to sex and weight, they were randomly divided into the blank control groups which comprise 10 guinea pigs and model group which comprise 50 guinea pigs. Blank control group were not subjected to any treatment. In model groups, each guinea pig was quantitatively smeared with 5% propranolol hydrochloride emulsion on its back skin of left auricle by 1 ml syringe, 0.1 ml/cm$^2$, twice a day (the interval is more than 6 hours), continued for 2 weeks. The skin samples of the auricle of two guinea pigs in the normal group and two in the model group were removed and obtained by operation in 24 hours after the last model establishment. The skin samples were fixed with 10% formaldehyde, stained with HE and observed under light microscope to evaluate the quality of the model.

48 guinea pigs in the model group were divided into 6 groups according to thickness of the auricle at the model side, 8 in each group. The experiment was divided into model group, Halometasone ointment active control group and sample 1-4 groups. Each sample group and positive control group were smeared with drug twice a day (the interval is more than 6 hours), continued for 2 weeks. The blank control was not subjected to any of treatment, the model group was administrated the same volume of propylene glycol. The thickness of the auricle was measured by vernier caliper every other day during the administration period, the hardness, skin color and scales change of the auricle were observed with naked eyes. After 2 weeks of administration, the skin of the left auricle of guinea pigs (on the administration side) was obtained by operation, fixed with 10% formaldehyde, embedded in paraffin and stained with HE, the changes of stratum corneum, stratum granulosum, stratum spinosm, stratum basale and lamina propria of the auricle skin were observed under light microscope. Significant difference between samples 2-3 and *Rumex madaio* (sample 1) were compared, after statistical treatment.

Result:

it was observed by the naked eye that the thickness of auricle from samples 1, 2, 3, 4 and positive Halometasone ointment group had become thinner and softer in varying degrees, the color tended to be normal, and the silver-white scales gradually disappeared on the 7th day after treatment. Compared with the model group, the thickness of auricle from each sample decreased significantly after 14 days of treatment. The results are shown in Table 1-1.

TABLE 1

Comparison of the effects of samples 1-4 groups on the auricle thickness of guinea pigs (X + SD, n = 8)

| Group | Administration site | Auricular thickness (mm) |
|---|---|---|
| Blank control | | 0.54 ± 0.01**** |
| Model control | back of auricle | 1.48 ± 0.39 |
| Positive Halometasone ointment | back of auricle | 0.51 ± 0.09**** |
| Sample 1 | back of auricle | 1.12 ± 0.39* |
| Sample 2 | back of auricle | 0.67 ± 0.26**# |
| Sample 3 | back of auricle | 0.76 ± 0.22**# |
| Sample 4 | back of auricle | 0.81 ± 0.30** |

Note:
(1) Compared with model control group, *$P < 0.05$, $P < 0.01$, *$P < 0.005$, **$P < 0.001$;
(2) Compared with sample 1 group, #$P < 0.05$; the same below.

In table 1-1, it is showed that the auricle thickness of guinea pig in propranolol hydrochloride model group was significantly higher than blank control group ($P < 0.001$), suggested that the model of auricle psoriasis-like skin lesion of guinea pig induced by propranolol hydrochloride was successful. Compared with the model of control group, samples 1, 2, 3 and 4 could significantly reduce the auricle thickness of model guinea pigs ($P < 0.05$ or $P < 0.01$); effect of samples 2 and 3 was significantly better than that of sample 1 ($P < 0.05$); compared with sample 1, sample 4 showed a certain trend of effect, but there was no statistical difference ($P > 0.05$).

Under light microscopy, auricle skins of normal guinea pig are a complete and homogeneous stratum corneum; the stratum granulosum is linear with obvious black granules on both sides, has about 1-3 layers; the stratum spinosm is mostly angular cells, and has about 4-6 layers; the stratum basale is a single layer of columnar cells, in which mitotic phase is reduced; the lamina propria is loose connective tissue; there is no significant abnormality in the hair follicles. In model group, cornification of stratum corneum was incomplete or excessive, stratum spinosm became thicker, and has about 5-8 layers, of which ⅔ of the nuclei were vacuolated; mitotic phase of stratum basale decreased, and there were more black-brown granulosa cells in cytoplasm of stratum basale in partial sections; congestion of lamina propria was found in individual sections. In each sample group, stratum corneum was relatively complete, and only individual animals showed uneven thickness or loose network; the stratum granulosum had more black-brown granules; the stratum spinosm became thinner, and has about 3-7 layers, with about ⅕ cell nucleus vacuolated (limitation); the mitotic phase of stratum basale cell decreased, no obvious brown granules were observed, and no obvious abnormalities were observed in submucosal hair follicles. The results suggest that samples 1-4 can significantly inhibit the psoriasis-like lesions of guinea pig auricle induced by propranolol hydrochloride, and indicated that samples 1-4 can significantly improve the pathological lesions of guinea pig auricle. The therapeutic effect of samples 2-4 was obviously better than sample 1. The specific results are shown in FIG. 1.

1.2 Effect on Scaly Epidermis on the Tails of Mice

Sixty healthy ICR mice (weight 18-22 g), half male and half female, were balancedly and randomly divided into 6 groups according to gender and body mass, each group has 10 mice. They were divided into matrix control group, positive control clobetasone propionate ointment group (0.02%) and samples 1-4 group. The tail skin of the mice in each group was smeared with drug twice a day (the interval is more than 6 hours). After 14 days of continuous administration, the mice were executed. The back epidermis about 1.5 cm from the tail root was taken and fixed with 10% formaldehyde, tissue sections were made routinely and HE stained. The changes of stratum corneum, stratum granulosum, stratum spinosm, dermis and hair follicle of mouse tail epidermis were observed under optical microscope. The number of scales with stratum granulosum formation in 100 scales was counted (where there are rows of granular layers on the scales epidermis between the orifices of two hair follicles, which will be counted as the scales with the formed granular layers). Histopathological examination showed that there were fewer granulosa cells in the tail epidermis of normal mice and the structure was normal. In the positive group, the stratum corneum was uneven, and some segments disappeared. There were many small particles in stratum granulosum, and the stratum spinosm was more 4-5 layers than the original. Samples 1-4, stratum corneum disappeared in some sections, more granules were found in the stratum granulosum, and stratum spinosm was more 3-4 layers than the original. The results showed that the formation of stratum granulosum of tail scales epidermal of mice in samples 1-4 and positive control groups were obviously induced after 2 weeks of external administration, it is suggested that each sample group had a good therapeutic effect on the main pathological manifestations such as imperfect cornification. The effect of samples 2-4 groups were more obvious than sample 1. The results are shown in Table 1-2.

TABLE 1-2

Effect of samples 1-4 on the formation of stratum granulosum in scale epidermis of mice tail (n = 10)

| Group | Administration site | Number of scales with stratum granulosum per 100 scales |
|---|---|---|
| Matrix control group | Tail | 11.2 ± 3.4 |
| Clobetasone propionate ointment | Tail | 21.5 ± 6.1*** |
| Sample 1 | Tail | 15.0 ± 3.2* |
| Sample 2 | Tail | 20.9 ± 3.4**# |
| Sample 3 | Tail | 19.9 ± 3.1**# |
| Sample 4 | Tail | 20.1 ± 3.8**# |

1.3 Inhibitory Effect on Auricular Inflammation in Mice Induced by Croton Oil

In severe psoriasis patients, because of the long-term skin lesions, also there are inflammation phenomena in skin lesions, such as redness, swelling, heat, pain and so on. Therefore, the inhibition of exudative inflammation by samples 1-4 was observed in the test, the comparison study over sample 1 also was conducted.

70 Kunming mice (weight 18-22 g), half male and half female. According to body weight, they were randomly divided into 7 groups, with 10 mice in each group. They were divided into blank control group, inflammation model group, positive Halometasone ointment group and samples 1-4 groups. Animals in each group were smeared with drug on the back of the right auricle of mice (left ear as self-control) daily, once a day, continued for 7 days. Auricle in the blank control group was not subjected to any treatment, and the croton oil model group was administrated drug matrix propylene glycol. One hour after the last administration, the subjects were washed with warm water. Except the blank control group, the right ears of mice in the remaining groups were smeared with 2% croton oil at 50 ul/mouse via syringes on the front and back sides respectively. Each group was smeared once again after three hours. The mice were executed one hour after the last administration, their ears were cut off, the ears slices were cut using a drill which has a diameter of 8 mm. The ears were weighed accurately and the weight difference between the two ears of its own is taken as the swelling value. After statistical treatment, t-test was carried out between groups to compare the significance of anti-inflammatory effect. The results are shown in tables 1-3.

TABLE 1-3

Inhibitory effects of samples 1-4 on auricular inflammation in mice induced by croton oil (X + SD, n = 10)

| Group | Administration site | Swelling value (mg) | Inhibition (%) |
|---|---|---|---|
| Blank control | | 1.03 ± 0.07 | |
| Model control | back of auricle | 38.56 ± 9.01 | |
| Positive Halometasone ointment | back of auricle | 8.25 ± 1.33**** | 78.60 |
| Sample 1 | back of auricle | 23.59 ± 6.72* | 38.82 |
| Sample 2 | back of auricle | 13.47 ± 4.39***## | 65.07 |
| Sample 3 | back of auricle | 16.46 ± 5.31**# | 58.05 |
| Sample 4 | back of auricle | 15.03 ± 5.86***# | 61.02 |

The results showed that samples 1-4 had significant inhibitory effect on exudative inflammation of mouse auricles induced by croton oil ($P<0.05$, $P<0.01$ or $P<0.005$ compared with model group), and the anti-inflammatory effects of samples 2, 3 and 4 were stronger than that of sample 1. Sample 2>Sample 3>Sample 4>Sample 1 in terms of the intensity of anti-inflammatory effect.

In summary, all the samples of the compositions of the present invention show obvious anti-psoriasis effect, and the effect of samples 2-4 are approximately similar.

Test 2. Comparative Study on the Treatment Effects of Samples 1-4 on Experimental Psoriasis Model Via Oral Administration Sample Preparation:

the dry powders of refined products of samples 1-4 in table 1 was selected and prepared into uniform suspension solution with purified water.

2.1 the Therapeutic Effect of Samples 1-4 on Psoriasis-Like Lesions of Auricle Skin in Guinea Pigs Induced by Propranolol Hydrochloride by Gavage Administration Sixty guinea pigs (weight is similar with experiment 1.1), the method of modeling and grouping were the same as experiment 1.1. "YinXieLing" was used as a positive control drug in this experiment via oral administration. During the administration period, the model group is not subjected to any treatment, which is acted as natural recovery control group of the skin lesion model; and each sample group was administrated intragastrically once a day, 0.333 ml/100 g body weight, continued for two weeks, during the administration period, the auricle thickness of each group was measured with vernier caliper every other day, and the color and hardness changes of auricle epidermis were observed. On the 14th day after administration, the skin of the left auricle of guinea pigs was dissected, fixed with 10% formaldehyde, paraffin-embedded, and HE stained. The changes of stratum corneum, stratum granulosum, stratum granulosum, stratum basale and lamina propria of the auricle skin were observed under light microscope.

Result:

it is observed by naked eye that the auricle thickness of guinea pigs in sample 1-4 and positive drug YinXieLing group became thinner and softer in varying degrees in 7 days after administration, and the skin color of guinea pigs become better than model group. It is observed by naked eye that the auricle thickness of each tested drug groups and YinXieLing group were significantly declined than that of model group in 14 days after administration of sample 1-4 and positive drug groups (see Table 2-1). It was showed by histopathological examination that the skin of the auricle in the blank control group was normal; extensive or focal parakeratosis could be observed on the auricle of the model group, accompanied by attenuation or disappearance of stratum granulosum. Most of the animals had the characteristics of stratum spinosm thickening, prolongation of epidermal apophysis, infiltration of dermal mononuclear and poly-morphonuclear cells, and telangiectasis. However, samples 1-3 showed significant improvement compared with model groups, and it was showed that cornification was relieved, inflammatory cell infiltration was reduced, and epidermis become thinner. The results of examination via light microscopy showed that blank control group and model control group were basically the same as those in experiment 1.1. The auricle thickness of guinea pigs in sample 1-4 groups was significantly lower than model group (P<0.01, P<0.005 or P<0.001). However, there was no statistical difference between samples 2-4 and sample 1. The results are shown in Table 2-1.

TABLE 2-1

Effect of samples 1-4 on psoriasis-like auricular lesion induced by propranolol hydrochloride in guinea pigs via intragastrical administration (X + SD, n = 8)

| Group | Dosage (g raw drug/kg) | Route of administration | Auricule thickness (mm) |
|---|---|---|---|
| Blank control | Purified water | i.g | 0.56 ± 0.11**** |
| Model control | Purified water | i.g | 1.51 ± 0.38 |
| YinXieLing | 10 | i.g | 0.68 ± 0.39** |
| Sample 1 | 10 | i.g | 0.92 ± 0.35** |
| Sample 2 | 10 | i.g | 0.78 ± 0.39*** |
| Sample 3 | 10 | i.g | 0.65 ± 0.38*** |
| Sample 4 | 10 | i.g | 0.60 ± 0.30**** |

Note:
Compared with model control group, *P < 0.05, P < 0.01, *P < 0.005, **P < 0.001, the same as below.

2.2 Effect of Samples 1-4 on the Scale Epidermis on Tails of Mice Via Intragastrical Administration Sixty ICR mice (weight 18-22 g), half male and half female. Except that the positive control drug was changed to YinXieLing, the animal grouping was the same as experiment 1.2. Animals in each group were administrated orally once a day, continued for 14 days. The mice were executed in 24 hours after the last administration. The back epidermis about 1.5 cm away from the tail root was taken and carried out the routine tissue sections and HE staining. The changes of stratum corneum, stratum granulosum, stratum spinosm, the dermis and hair follicle of mouse tail epidermis were observed by optical microscope. The number of scales with stratum granulosum formation in 100 scales was counted. The results showed that there was a natural lack of stratum granulosum in the scaly epidermis of normal mice, keratinocytes in stratum corneum of the scaly epidermis of mice tail retained nuclei, while granulosa cells in the stratum granulosum were absent. There were only a few granulosa cells in the hair follicle, and the epidermis was thinner. the tested substance i.e. Samples 1, 2, 3 and 4 had obvious promoting effects on the formation of epidermal stratum granulosum of mouse tail scales (P<0.05 or P<0.01 compared with the blank control group). These results suggest that samples 1-4 had obvious therapeutic effect on the main pathological manifestations of tail such as cornification incompleteness etc. in mice, and the effect of samples 2 and 3 is better than samples 1 and 4. The results are shown in Table 2-2.

TABLE 2-2

Effect of samples 1-4 on the formation of stratum granulosum in the tail epidermis of mice via intragastrical administration (X + sd, n = 10)

| Group | Dosage (g raw drug/kg) | Route of administration | Number of scales which having stratum granulosum formation per 100 scales |
|---|---|---|---|
| Solvent control group | — | i.g | 11.9 ± 3.6 |
| YinXieLing | 15.0 | i.g | 23.5 ± 7.21*** |
| Sample 1 | 15.0 | i.g | 15.8 ± 4.6* |
| Sample 2 | 15.0 | i.g | 19.9 ± 6.4** |
| Sample 3 | 15.0 | i.g | 19.7 ± 6.1** |
| Sample 4 | 15.0 | i.g | 15.9 ± 4.7* |

2.3 Anti-Inflammatory Effect of Samples 1-4 on Auricular Inflammation in Mice Induced by Croton Oil 70 Kunming male mice (weight 18-22 g) were grouped according to the same way in experiment 1.3. Each groups were administrated intragastrically every day, continued for 7 days. One hour after the last administration, except for the blank control group, the remaining groups were smeared with 50 UL 2% of croton oil with syringes on the front and back sides of mice ears, three hours later, each group was administrated once again. One hour after the last administration, the mice were executed, their ears were cut off, and the ear slices were made with a perforator with 8 mm diameter, weighed accurately, and the difference between the two ears of its own was taken as the swelling value. After statistical treatment, t-test was carried out among groups to compare the significance of anti-inflammatory effect. The results are shown in Table 2-3.

TABLE 2-3 effects of samples 1-4 on auricular inflammation
in mice induced by croton oil via intragastrical
administration (X + SD, n = 10)

| Group | Dosage (g raw drug/kg) | Route of administration | Swelling value (mg) | Inhibition of inflammation (%) |
|---|---|---|---|---|
| Blank control | | i.g | 1.63 ± 0.05**** | |
| Model control | | i.g | 33.11 ± 9.87 | |
| YinXieLing | 15.0 | i.g | 17.32 ± 5.33**** | 47.69 |
| Sample 1 | 15.0 | i.g | 23.78 ± 6.72* | 28.18 |
| Sample 2 | 15.0 | i.g | 18.47 ± 6.19** | 44.22 |
| Sample 3 | 15.0 | i.g | 19.39 ± 5.87*** | 41.44 |
| Sample 4 | 15.0 | i.g | 16.25 ± 5.06***# | 50.92 |

Table 2-3 showed that samples 1-4 were intragastrically administrated for 7 days, and have a significant inhibitory action on inflammation of mice auricle induced by croton oil. ($P<0.05$, $P<0.01$ or $P<0.005$). Compared with Sample 1, $P<0.05$ in sample 4, the intensity of anti-inflammatory effect of each sample was sample 4>sample 2>sample 3>sample 1.

The invention claimed is:

1. A traditional Chinese medicine composition effective for treating psoriasis, consisting of:
    20-80 parts (w/w) extract of dry roots of a plant of genus *Rumex*, wherein the plant is selected from the group consisting of *R. patientia, R. crispus, R. nepalensis, R. dentatus, R. obtosifolius, R. japonicus, R. acetosa, R. trisetifer, R. chalepensis, R. gmehnii*, and *R. hastatus*; and
    20-80 parts (w/w) of dry roots of *Sophora flavescens* Ait, prepared by a method comprising:
        preparing the extracts wherein individual components having corresponding weight parts in the composition are obtained respectively, and broken into coarse grains, mixed uniformly, the resulting mixture is immersed in a solvent of water or 50-100% pharmaceutical ethanol at about 40 degrees for about 0.5 to 1 hour, then is extracted for three times by heating refluxing, each extraction time is 1-2 hours and the total amount of solvents is 15-20 (L/kg); the reflux solution is subjected to sedimentation separation under atmospheric pressure, treated by one or two of suction filtration or centrifugation (4000 rpm, 30 min) to obtain the extract solution; solvents in the extract solution are recovered by treatment of one or two selected from evaporation concentration under reduced pressure or film concentration at 60° C. or below to provide a concentrate; and the concentrate is dried under vacuum at 60° C. or below to provide the extracts; the extract is pulverized into fine powder, which is prepared into suitable formulations;
        preparing refined products, including:
            refining the extracts obtained by using ethanol, wherein firstly includes being treated by water sedimentation, the water-insoluble precipitated after treating is dried under vacuum and stored, the remaining aqueous solution is separated by any one of macroporous adsorption resin columns selected from AB-8, SP-825, or X-5, in which the diameter-length ratio of the resin column is 1:6-1:10, the column is eluted with water at a flow rate of 2-9 BV/h to remove impurities such as saccharides and inorganic salts, and then is gradiently eluted with 5%-100% ethanol at a flow rate of 3-10 BV/h, the eluate is collected, concentrated under reduced pressure, vacuum dried and combined with the water insoluble precipitates to provide the refined products; or
            refining method of water extracts extracted by water, wherein the water extracts are precipitated with several times of ethanol to provide ethanol precipitate and ethanol soluble substance, the macromolecular impurities in the ethanol precipitate are discarded; the water-insoluble substance in the ethanol-soluble portion is dried and stored; the water-insoluble substance is subjected to macroporous resin adsorption or polyamide chromatography to remove small molecular sugars and inorganic salts, or is treated by membrane separation technology to remove impurities; when the impurities are removed by macroporous adsorption resin in which a column having a diameter-length ratio of 1:6 to 1:10 is used, the column is eluted with water at a flow rate of 5-2 BV/h to remove small molecular saccharides and inorganic salts, and then eluted gradiently with 5%-100% ethanol at the flow rate of 3-10 BV/h; the eluate is collected, concentrated under reduced pressure, dried under vacuum, and combined with the dry substance of the water insoluble substance to provide the refined products.

2. The Chinese medicine composition according to claim 1, wherein the composition consists of 35-65 parts (w/w) *Rumex madaio* and 35-65 parts (w/w) Radix *sophora flavescens*.

3. The Chinese medicine composition according to claim 1, wherein the composition consist of 30-50 parts (w/w) *Rumex madaio* and 30-50 parts (w/w) Radix *sophora flavescens*.

4. The Chinese medicine composition according to claim 1, wherein the plant of genus *Rumex* is selected from the group consisting of *R. patientia, R. crispus, R. nepalensis, R. japonicus, R. dentatus*, and *R. obtosifolius*.

5. The traditional Chinese medicine composition according to claim 1, wherein the composition is formulated as a gel, an ointment, a cream, a film coating agent, a lotion, a liniment, an aerosol, a spray or plaster, a tablet, a pill, a capsule, or a dropping pill.

* * * * *